Oct. 16, 1962 D. H. MOREY, JR Plant Pat. 2,184
ROSE PLANT
Filed Nov. 29, 1961
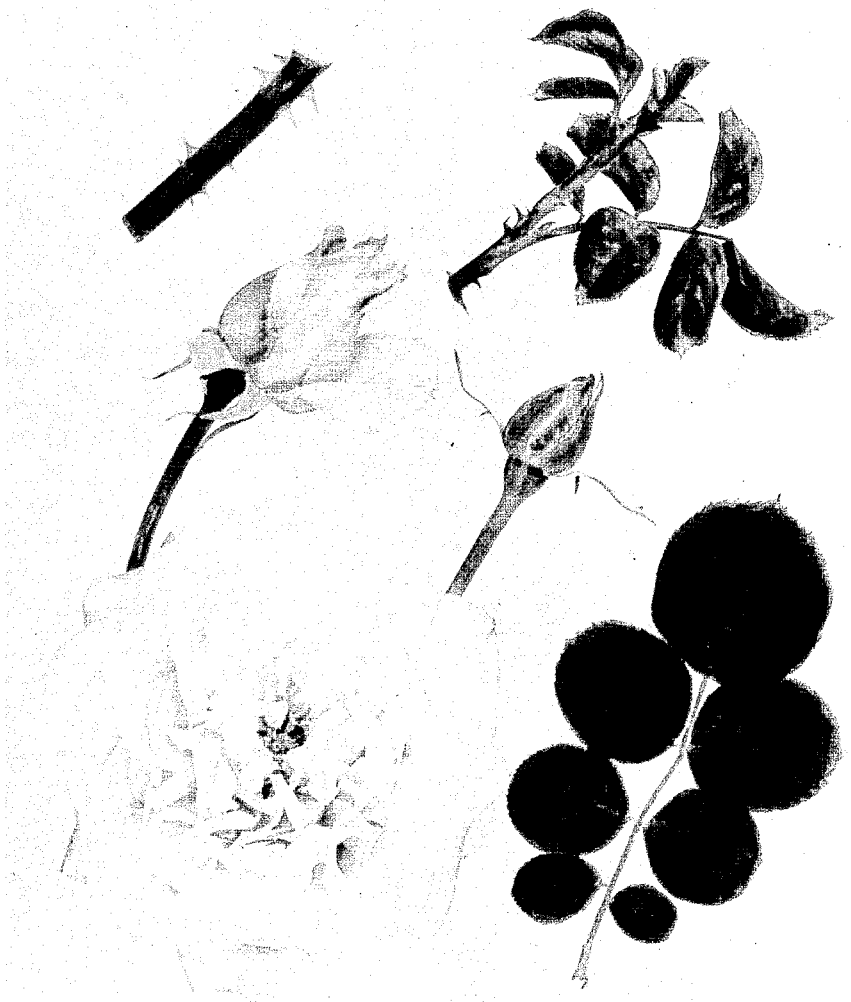
Inventor
Dennison H. Morey, Jr
By: Robb & Robb
Attorneys United States Patent Office Plant Pat. 2,184
Patented Oct. 16, 1962

2,184
ROSE PLANT

Dennison H. Morey, Jr., Pleasanton, Calif., assignor to Jackson & Perkins Company, Newark, N.Y., a corporation of New York Filed Nov. 29, 1961, Ser. No. 155,876
1 Claim. (Cl. 47—61)

The present invention relates to a new and distinct variety of rose plant of the hybrid tea class, which was originated by me by crossing the variety "Rapture" (unpatented) with an unnamed and unpatented climbing hybrid tea seedling.

The primary objective of this breeding was to produce a new hybrid tea rose variety having more vigorous growing habits. This objective was achieved, along with other desirable improvements, as evidenced by the following unique combination of characteristics which are outstanding in the new variety and which distinguish it from its parents, as well as from all other varieties of which I am aware:

(1) A tall and vigorous habit of growth;

(2) Attractive and interesting half-blown buds which are suitable for flower show exhibitions;

(3) Large flowers of hybrid tea type; and (4) A distinctive, attractive and unusual general color tonality of the open flowers corresponding to Thulite Pink, faintly overcast with Spinel Pink.

Asexual reproduction of my new variety by budding, as performed at Pleasanton, California, and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Rapture."
*Pollen parent.*—An unnamed climbing hybrid tea seedling.

Classification:
*Botanic.*—Hybrid tea.
*Commercial.*—Hybrid tea.

*Flower*

(Observations made from specimens grown outdoors at Newark, New York, during the early afternoon in the early part of the month of August.)

Blooming habit: Recurrent—continuous.

Bud:
*Size.*—Large.
*Form.*—Ovoid; is not affected by wet or hot weather.
*Color.*—When sepals first divide—Bordeaux, Plate 12. When petals begin to unfurl—Bordeaux, Plate 12, lightly overcast with Pomegranate Purple, Plate 12. When half-blown: inside of petals—Begonia Rose, Plate 1, lightly overcast with Eugenia Red, Plate 13; reverse of petals—Carmine, Plate 1, lightly overcast with Eugenia Red, Plate 13.
*Sepals.*—Slightly branched; curl back when petals begin to unfurl. Color: inside—Olivine, Plate 32; outside—Bice Green, Plate 17.
*Calyx.*—Color—Bice Green, Plate 17. Shape—apple. Size—small. Aspect—smooth. Odor when rubbed—none.
*Peduncle.* — Length — medium. Aspect — rough. Strength—erect; heavy. Color—Light Bice Green, Plate 17.
*Opening.*—Opens up well; is not affected by adverse weather conditions.

Bloom:
*Size.*—Very large. Average size when fully expanded—7 inches.
*Borne.*—Singly and several together.
*Stems.*—Long; strong.
*Form (when first open).*—Cupped. Permanence—flattens.
*Petalage.*—Very double (many petals and stamens hidden). Number of petals under normal conditions—from 45 to 50.
*Color.*—Center of flower—Spinel Pink, Plate 26, very lightly overcast with Thulite Pink, Plate 26. Outer petals—Thulite Pink, Plate 26, with outer edge of petals lightly overcast with Spinel Pink, Plate 26. Base of petals (aiglet)—Pinard Yellow, Plate 4. Inside of petals—Thulite Pink, Plate 26, faintly overcast with Spinel Pink, Plate 26. Reverse of petals—Rose Pink, Plate 12, with outer edge of petals lightly overcast with Deep Rose Pink, Plate 12. General tonality from a distance—Thulite Pink, Plate 26, lightly overcast with Spinel Pink, Plate 26.
*Discoloration.*—General tonality at end of first day—Spinel Pink, Plate 26, overcast with Thulite Pink, Plate 26. Second day—Thulite Pink, Plate 26, very lightly overcast with Spinel Pink, Plate 26. Third day—Thulite Pink, Plate 26, very lightly overcast with Spinel Pink, Plate 26.

Petals:
*Texture.*—Leathery; is not affected by wet or hot weather.
*Apperance.*—Inside—satiny. Outside—shiny.
*Form.*—Oval.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—long. As cut flower—long.

*Genital Organs*

Stamens, anthers: Medium size; many; regularly arranged around styles. Color—Apricot Buff, Plate 14.
Stamens, filaments (threads): Medium length. Color—Shell Pink, Plate 28.
Pollen: Color—Salmon-Buff, Plate 14.
Styles: Loosely separated; uneven length; medium length; thin.
Stigmas: Color—Capucine Buff, Plate 3.
Ovaries: All enclosed in calyx.
Hips: None.
Seeds: None.

*Plant*

Form: Bush.
Growth: Vigorous; upright.
Foliage: Compound of 3–7 leaflets.
*Size.*—Large.
*Quantity.*—Abundant.
*Color.*—New foliage: upper side—Oxblood Red, Plate 1, with center lightly overcast with Carmine, Plate 1; under side—Bordeaux, Plate 12. Old foliage: upper side—Dark Yellowish Green, Plate 18; under side—Jade Green, Plate 31.
*Shape.*—Oval.
*Texture.*—Upper side—leathery. Under side—smooth.

*Ribs and veins.*—Ordinary.
*Edge.*—Serrated (saw-toothed).
*Serration.*—Both double and single; small.
*Leaf stem.*—Color—Chromium Green, Plate 32. Under side—smooth.
*Stipules.*—Medium length; smooth.

Wood:

*New wood.*—Color—Van Dyke Red, Plate 13. Bark—smooth.
*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; hooked downward. Color (when young)—Van Dyke Red, Plate 13. Position—irregular.

*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by the unique combination of a tall and vigorous habit of growth, attractive and interesting half-blown buds which are suitable for flower show exhibition, large flowers of hybrid tea type, and an attractive, distinctive and unusual general color tonality of the open flowers corresponding to Thulite Pink, faintly overcast with Spinel Pink.

No references cited.